United States Patent [19]

Fournier et al.

[11] Patent Number: 4,549,440

[45] Date of Patent: Oct. 29, 1985

[54] FLUID SAMPLING VALVE

[75] Inventors: Paul J. E. Fournier, Jackson; Russell L. Rogers, Munith, both of Mich.

[73] Assignee: Aeroquip Corporation, Jackson, Mich.

[21] Appl. No.: 594,843

[22] Filed: Mar. 29, 1984

Related U.S. Application Data

[63] Continuation-in-part of Ser. No. 450,370, Dec. 16, 1982, Pat. No. 4,484,482.

[51] Int. Cl.⁴ .............................................. G01N 1/10
[52] U.S. Cl. .............................. 73/863.85; 73/863.86; 210/235
[58] Field of Search ............ 73/863.72, 863.81, 863.85, 73/863.86, 864.23, 864.24; 141/329, 351; 210/233–235

[56] References Cited

U.S. PATENT DOCUMENTS

| 2,544,244 | 3/1951 | Vokes | 210/234 |
|---|---|---|---|
| 2,630,919 | 3/1953 | Tyler | 210/233 |
| 2,786,355 | 3/1957 | Day et al. | 73/863.81 |
| 2,932,400 | 4/1960 | Scavuzzo | 210/235 |
| 3,198,016 | 8/1965 | Poorman | 73/863.86 |
| 3,638,499 | 2/1972 | Saint-Andre | 73/863.86 |
| 3,715,032 | 2/1973 | Nicko | 210/234 X |
| 3,852,196 | 12/1974 | Szpur | 210/234 X |
| 4,289,027 | 9/1981 | Gleaves et al. | 73/863.86 X |
| 4,484,482 | 11/1984 | Fournier et al. | 73/863.85 |

FOREIGN PATENT DOCUMENTS

| 1079994 | 8/1967 | United Kingdom | 73/863.86 |
| 549706 | 5/1977 | U.S.S.R. | 73/863.86 |

Primary Examiner—Robert Spitzer
Attorney, Agent, or Firm—Beaman & Beaman

[57] ABSTRACT

The invention pertains to a valve particularly suitable for sampling internal combustion engine lubricating oil while under pressure being used within the engine and consists of a valve body placed within a pressurized oil conduit. The body includes an orifice having a valve movable between open and closed positions by a sample collecting receptacle wherein one hand operation is readily achieved. The valve includes a proboscis suitable for piercing the sample receptacle diaphragm, and a spring produces a positive biasing force on the valve toward the closed position. A pressure balancing piston connected to the valve balances the force necessary for valve operation due to internal pressure. A removable cover protects the valve and proboscis when not in use.

11 Claims, 4 Drawing Figures

FLUID SAMPLING VALVE

BACKGROUND OF THE INVENTION

This application is a continuation-in-part of the assignee's U.S. Ser. No. 450,370 filed Dec. 16, 1982, now U.S. Pat. No. 4,484,482.

To achieve the most efficient utilization of the oils used in internal combustion engines and drive systems, hydrostatic transmissions and pressurized hydraulic circuits, it is known to monitor and analyze the condition of the oil wherein its lubricative qualities, acidic content, the presence of foreign matter and colloidal suspensions, moisture content, and other characteristics can be determined by analysis, and by closely monitoring the condition of the oil replacement is made only when necessary, rather than on a duration or engine use basis, as is normal.

It has been found that many oils used in engines and transmissions are changed at a much greater frequency than is necessary, and in some extra heavy duty applications, oils should be replaced at a more frequent interval than normal. By the monitoring and analyzing of oils while in use large oil users, such as the armed forces, truck fleet operators, and automobile fleet operators, can experience substantial savings in both oil consumption and engine and transmission wear.

In the past, the monitoring and analyzing of engine and transmission oils has been troublesome due to the lack of a convenient method of obtaining oil samples. By the use of syringes, oil may be removed through dipstick tubes, and the like, but special types of syringes are required and this apparatus is only usable on internal combustion engines, and may not be readily used with transmissions or other lubricated components not utilizing dipsticks and the like.

Further, as it is absolutely necessary that oil samples removed for analyzing and monitoring purposes must truly reflect the conditions of the oil in use, contamination of the samples during procurement of the samples must be prevented and prior oil sampling apparatus and systems have not been consistently successful in assuring sample integrity.

While the oil sampling apparatus disclosed in the application identified above overcomes the aforementioned problems, such apparatus cannot be used in lubricating or hydraulic systems of high pressure in that valve actuation controlling flow of the oil into the sampling container is manually actuated, and with fluid systems of high pressure, manual actuation of the valve may not be possible.

It is an object of the invention to provide an oil sampling valve for use with internal combustion engines, transmission, hydraulic circuits, and the like, wherein oil samples may be readily obtained from high pressure circuits without the use of special tools, equipment or skills.

Another object of the invention is to provide an oil sampling valve for use with internal combustion engines and the like wherein one hand operation is achieved even with high pressure circuits as the control of the valve is by means of the sample collecting receptacle.

A further object of the invention is to provide an oil sampling valve which may be readily incorporated into the high pressure oil circuits of an internal combustion engine or the like, and wherein the components thereof may be protected against damage and contamination when not in use.

The oil sampling valve in accord with the invention includes a body which is incorporated into the oil circuit of the engine, transmission, or other system whose oil is to be monitored and analyzed. The valve includes a body having a passage defined therein wherein the passage forms a part of the oil circuit.

An orifice defined in the body communicates with the body passage and a movable valve controls oil flow through the orifice. The valve is movable between open and closed conditions, and the valve is actuated by a disk which is selectively engaged by the opening of the sampling container or receptacle. By placing the receptacle against the valve operator and displacing the valve by overcoming a spring biasing the valve toward the closed position the valve is opened permitting oil flow through the orifice into the receptacle.

The valve structure is in the form of a piston having a pressure face exposed to the pressure of the oil circuit, and the oil pressure biases the valve toward a closed condition. To balance the force imposed upon the valve by the fluid pressure, the valve includes a balancing piston in opposed relationship to the valve piston structure, and by utilizing slightly different area pressure faces exposed to the fluid pressure, only a relatively small axial force is required to displace the valve regardless of the value of the fluid pressure within the body.

The oil collection receptacle often includes a membrane closing the receptacle opening, and the valve includes a sharpened proboscis which readily penetrates the membrane as the receptacle is moved toward engagement with the valve actuator. Thus, merely by holding the collecting receptacle, the operator in the act of positioning the receptacle causes the proboscis to pierce the receptacle membrane and the receptacle controls the flow of the oil sample thereinto.

Removal of the sampling receptacle from the valve actuator permits the valve to be shifted to the closed position by its spring, and the proboscis and valve are protected against contamination when not in use by means of a removable cover threaded to the valve body.

The sampling valve constructed in accord with the invention is of a relatively simple configuration and form, readily manufacturable, and the construction is such as to be relatively trouble free in operation.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
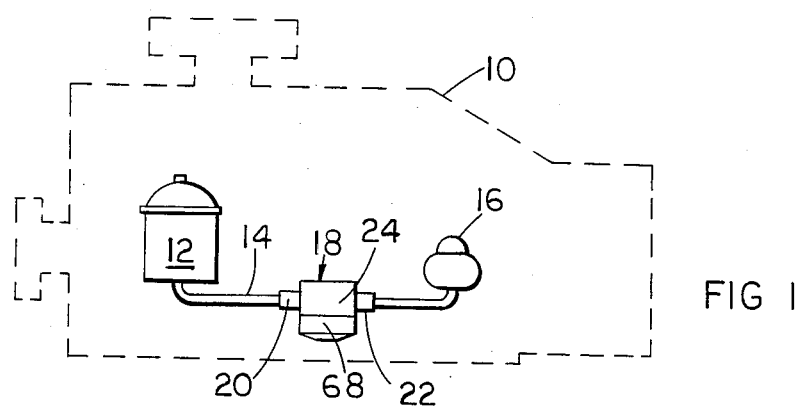
FIG. 1 is a schematic view of a typical installation of sampling valve in accord with the invention as used with an internal combustion engine, the engine being shown in dotted lines.

With reference to FIG. 1, an internal combustion engine is schematically represented in dotted lines at 10. The engine oil filter is shown at 12, and the oil filter includes a pressurized conduit 14 associated therewith. The conduit 14 is connected to the engine fitting 16 communicating with the internal engine components wherein all of the engine lubricating oil passes through the conduit 14 during engine operation. The oil sampling valve 18 is mounted within the conduit 14 by a pair of fittings 20 and 22, wherein the engine lubricating oil is circulated through the valve 18.

Of course, it is to be appreciated that the oil sampling valve 18 may be located within any pressurized fluid circuit for the purpose of readily obtaining a sample of the circuit oil, and the sampling valve of the invention may be readily employed with transmissions, general purpose hydraulic circuits, or the like.

The sampling valve 18 includes a body 24 having a passage 26 defined therethrough. The passage includes a threaded inlet port 28, and a threaded outlet port 30, the conduit fitting 20 being threaded into port 28, while the conduit fitting 22 mates with the threads of port 30.

The body 24 includes a threaded circular opening 32 which receives the threaded central hub 34 of the skirt 36. The skirt is sealed to the body by O-ring 38 and is externally threaded at 40.

The skirt hub 34 is provided with a coaxial orifice 42 which communicates with the passage 26, and the orifice receives the valve 44 therein. The valve 44 includes shouldered portions for receiving O-ring 46 therebetween, and the ring 46 seals the valve with respect to the orifice when the valve is in the closed condition shown in FIGS. 2 and 3.

The valve 44 includes a downwardly extending circular proboscis 48 which terminates at its lower end in the oblique surface 50 defining a sharp tip 52. Internally, the proboscis 48 includes a passage 54 intersecting surface 50, and a radial passage 56 defined in the valve intersects the passage 54 and the exterior of the valve, as readily appreciated in FIG. 3. The passage 56 is located "below" the O-ring 46, and will be sealed with respect to the passage 26 when the valve is in the closed position.

The valve 44 includes an upwardly disposed extension 45 which terminates in a piston head 47 reciprocal within cylindrical chamber 49 defined in body 24. The piston head is sealed to the chamber by an O-ring. The area of the pressure face of piston head 47 exposed to the fluid pressure within passage 26 is slightly less than the pressure face of valve 44 so exposed, and the passage 54 extends upwardly through piston head 47 to communicate with chamber 49 to prevent a pressure buildup in the chamber.

A valve actuator disk 58 surrounds the proboscis 48 and is attached thereto and axially affixed thereon by means of the proboscis shoulder 60, and a snap ring 62 received within a groove defined on the proboscis. A spring steel wave washer 64 is interposed between the actuator disk 58 and the skirt radial portion imposing a downward biasing force on the disk which tends to translate the valve 44 to the closed condition of FIGS. 2 and 3.

The skirt 36 defines a chamber 66 in which the actuator disk 58, proboscis 48, and spring washer 64 are located, and this chamber is enclosed when the sampling valve is not in use, by means of a cover or cap 68 attached to the body 24 by the chain lanyard 70. The cover 68 is internally threaded at 72 for threaded engagement with the skirt threads 40 and as noted in FIGS. 1-3, the cap or cover 68 when attached to the skirt threads encloses the valve proboscis and protects the chamber 66, and associated components, against contamination.

Figure 2:
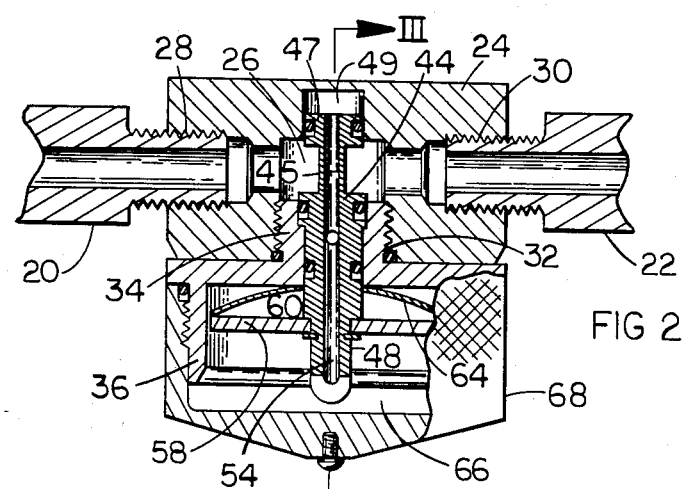
FIG. 2 is an elevational, sectional, detail view of a sampling valve in accord with the invention with the valve in the closed condition.
Figure 3:
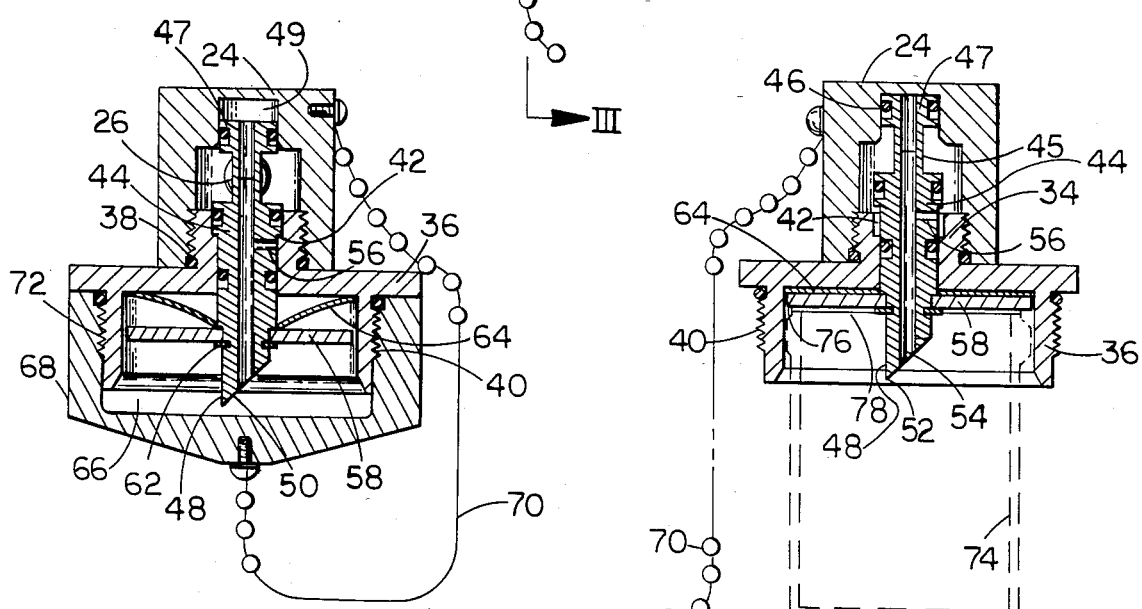
FIG. 3 is an elevational, sectional view of the apparatus as taken along Section III—III of FIG. 2.

Installation of the sampling valve 18 within an oil conduit 14 is readily achieved by a mechanic of normal skills in that the conduit is severed, flanged and conventional fittings 20 and 22 placed thereon. Upon the fittings being threaded into the body ports the integrity of the oil circuit is retained, and oil flow through the conduit 14 and sampling valve 18 is unrestricted. Under normal conditions the sampling valve components will be as shown in FIGS. 2 and 3, the spring wave washer 64 maintaining the valve 44 in the closed condition, and the cover 68 is fully threaded upon the skirt threads 40 to enclose the chamber 66.

When it is desired to collect an oil sample, the engine will normally be running wherein a pressure is maintained within the conduit 14, and the cover 68 is removed by unthreading from the skirt 36. The collection receptacle 74, shown in dotted lines in FIG. 4, may merely consist of a bottle or similar container having an upper opening defined by edge 76. Usually, the sampling container will have been thoroughly cleaned, or sterilized, and the state of cleanliness maintained by sealing a membrane 78 across the receptacle opening upon the edge 76.

Figure 4:
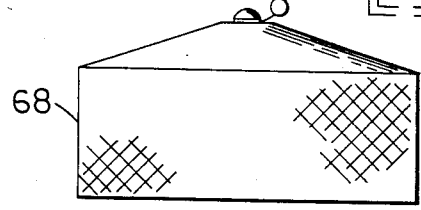
FIG. 4 is an elevational, sectional view similar to FIG. 3 illustrating the sampling receptacle in position and the valve in the open condition.

After the cover 68 has been removed, the operator merely holds the receptacle in one hand, moves the receptacle 74 upwardly toward the valve actuating disk 58, and as the receptacle approaches the disk the proboscis 48 will engage and penetrate the membrane. Further movement of the receptacle toward the valve body causes the receptacle edge to engage the valve actuator disk 58, and further pressure exerted upon the disk by the receptacle displaces the valve 44 upwardly toward passage 26 to the open condition as shown in FIG. 4. The upward displacement of the valve places the passage in communication with the passage 54 permitting oil within the passage 26 to flow through the lower end of the proboscis into the receptacle 74.

The receptacle is maintained against the disk 58, compressing the spring washer 64, to hold the valve 44 open until the desired amount of oil is accumulated within the receptacle. Thereupon, the operator merely lowers the receptacle away from the disk 58, and the positive force exerted by the spring washer, and the pressure within passage 26, returns the valve 44 to its closed condition without spillage. The cover 68 is then screwed upon threads 40, and a cap, not shown, is placed upon the receptacle and the receptacle may be taken to the laboratory for analysis.

From the above, it will be appreciated that the oil sampling valve of the invention requires no tools during operation. The entire sample collecting procedure can be accomplished by the use of only one hand, and the valve automatically closes when the receptacle is removed. The use of the proboscis eliminates the need for a membrane piercing tool which might contaminate the fluid, and the proboscis directs the fluid to the bottom of the sampling container reducing the likelihood of spillage or injury to the operator from contact with hot oil.

The use of the piston head 47 balances the fluid pressure imposed on valve 44 and the apparatus may be used to sample oil in high pressure circuits without excessive manual effort.

The protective cap or cover 68 serves as a secondary seal in the event the valve 44 should leak or fail, and the use of the cover prevents the chamber 66 from being contaminated with the dust and dirt usually surrounding internal combustion engines.

It will be appreciated that the aforedescribed oil sampling valve structure meets the objects and advantages sought, and it is appreciated that various modifications to the inventive concepts may be apparent to those skilled in the art without departing from the spirit and scope of the invention.

We claim:

1. A fluid sampling valve for internal combustion engines and the like, comprising, in combination, a body, a passage defined in said body having an inlet and an outlet, a valve element receiving orifice defined in said body intersecting said passage, a valve element within said orifice movable between open and closed positions wherein fluid within said passage flows through said orifice when said valve element is in said open position, pressure balancing means defined on said valve element in communication with said passage and sample collecting container engaging means defined upon said valve element for actuation of said valve element between said open and closed positions by a sample collecting container.

2. In a fluid sampling valve as in claim 1, sealing means defined adjacent said orifice, said valve element engaging said sealing means at said closed position.

3. In a fluid sampling valve as in claim 2, said valve element including a proboscis having a free end, a flow passage defined within said valve element and proboscis having an inlet adjacent said sealing means and an outlet intersecting said free end, fluid flowing through said orifice flowing through said flow passage.

4. In a fluid sampling valve as in claim 3, a membrane piercing surface defined upon said proboscis free end.

5. In a fluid sampling valve as in claim 1, said container engaging means comprising a disk mounted upon said valve element.

6. In a fluid sampling valve as in claim 5, a spring mounted upon said body biasing said valve element toward said closed position.

7. In a fluid sampling valve as in claim 3, a chamber defined upon said body, said proboscis and container engaging means being located within said chamber, cover retaining means defined upon said body, and a cover selectively engagable with said retaining means for selectively enclosing said chamber.

8. In a fluid sampling valve as in claim 7, said cover retaining means comprising a first thread defined upon said body, said cover having a second thread defined thereon cooperable with said first thread.

9. In a fluid sampling valve as in claim 1, said pressure balancing means comprising a piston head defined on said valve element having a pressure face in communcation with said passage.

10. In a fluid sampling valve as in claim 9, said valve element having a pressure face in communication with said passage, said piston head pressure face being slightly less in area than the pressure face of said valve element.

11. In a fluid sampling valve as in claim 9, said piston head pressure face producing a force on said valve element tending to move said valve element toward said open position.

* * * * *